United States Patent [19]

Stewart

[11] Patent Number: 4,674,473
[45] Date of Patent: Jun. 23, 1987

[54] CORE SLABBING METHOD

[75] Inventor: Ross W. Stewart, Dhahran, Saudi Arabia

[73] Assignee: Arabian American Oil Company, Dhahran, Saudi Arabia

[21] Appl. No.: 873,184

[22] Filed: Aug. 4, 1986

Related U.S. Application Data

[62] Division of Ser. No. 556,797, Dec. 1, 1983, Pat. No. 4,628,894.

[51] Int. Cl.$^4$ .............................................. B28D 1/00
[52] U.S. Cl. ........................................ 125/1; 264/139; 83/167; 83/874; 53/435; 53/452; 125/21
[58] Field of Search ...................... 125/13 R, 16 R, 21, 125/1; 83/102.1, 870–874, 167; 51/73 R; 264/139; 53/435, 452

[56] References Cited

U.S. PATENT DOCUMENTS

| 1,806,862 | 5/1931 | Owen | 125/13 R |
| 1,897,425 | 2/1933 | Fritts | 83/872 |
| 2,377,437 | 6/1945 | Martin | 125/13 R |
| 2,924,050 | 2/1960 | Barron | 125/21 |
| 3,008,462 | 11/1961 | Williams | 125/13 R |
| 3,171,450 | 3/1965 | Boullet | 83/102.1 |
| 3,585,980 | 6/1971 | Mellor | 51/273 |
| 3,662,733 | 5/1972 | Okamoto | 125/13 R |
| 4,230,007 | 10/1980 | Grote | 83/874 |
| 4,270,423 | 6/1981 | Angelo | 83/102.1 |

FOREIGN PATENT DOCUMENTS

| 520020 | 3/1955 | Italy | 125/21 |
| 4727200 | 6/1969 | Japan | 83/870 |

Primary Examiner—Harold D. Whitehead
Attorney, Agent, or Firm—Thomas E. Spath

[57] ABSTRACT

A geological core sample is slabbed by advancing the sample against a horizontally oriented bandsaw blade. A receiving tray positioned immediately adjacent and to the rear of the bandsaw blade provides continuous support to the upper portion of the slab as it is cut from the sample and maintains the integrity of friable and unconsolidated materials.

13 Claims, 5 Drawing Figures

CORE SLABBING METHOD

This is a division of co-pending application Ser. No. 556,797 filed on Dec. 1, 1983 and now U.S. Pat. No. 4,628,894 issued Dec. 16, 1986.

BACKGROUND OF THE INVENTION

1. Field of the Invention

The present invention relates to a method and apparatus for exposing an interior surface of a stratigraphic sample, and in particular to a method and apparatus which leaves undisturbed the physical and chemical properties of the exposed interior stratigraphy of such sample.

2. Description of the Prior Art

The study of geological strata generally involves the on-site collection of geological samples and the removal of these samples to remote laboratories for analysis. The geological material is typically collected in the form of an elongated cylindrical core which is encased within a plastic sleeve or tube that is positioned within the boring shaft or pipe. (The term "sample" will hereinafter be used to refer collectively to both such a core and the sleeve in which it is enclosed.) Once in the laboratory, the sample is split along its longitudinal axis to expose the interior stratigraphic profile of the core material in a process which is commonly referred to as "slabbing". The longitudinal section thereby split off from the sample comprising the core material, with or without the section of the sleeve or tube is referred to as a "slab".

The accuracy of the data acquired from the laboratory analysis of the slab depends to a large extent upon the degree to which the interior stratigraphic profile is left undisturbed by the slabbing process. Disturbance to the interior stratigraphy poses a particular problem when the core is composed of material which is "friable" (i.e., brittle) or "unconsolidated" (i.e., composed of loose gravel, sand or the like).

Several prior art methods have been employed for slabbing samples. In one such method the sample is first oriented so that its longitudinal axis is horizontal. A small horizontal knife blade is then passed several times through one side of the sample in a direction parallel to the longitudinal axis. On the initial pass of the knife blade only the plastic tube surrounding the core is cut. On each subsequent pass the knife is guided slightly closer to the central axis of the core, the objective being to divide the core gradually so as not to disturb its internal composition. After one side of the sample has been completely divided, the sample is rotated 180 about its longitudinal axis and the slicing procedure is repeated on the opposite side. The sample is then pulled apart into equal halves, thereby exposing the interior stratigraphic profile.

Among the major disadvantages of the above method are the extensive amount of time required to slab each sample and the limitation of the method to cores of soft material, such as mud, sand, clays and the like. This limitation is due to the fact that the small blade used in this process is incapable of splitting the larger rock fragments which may be found in the core. Instead the blade merely pushes these rock fragments through the core, causing undesired disturbance to the material comprising the core and thereby to the stratigraphic profile. In addition, this method provides no mechanism for supporting the freshly cut core material after each pass of the knife blade. If the core material is comprised of loose sand or gravel, the freshly cut interior surface will merely collapse as the knife passes through the core. This method therefore can not be used to slab unconsolidated core material.

There is a variation of the above method in which a very broad knife blade is passed once through the entire sample. The knife blade is sufficiently broad so that as the slab is separated from the sample it is supported on the knife blade itself, thereby enabling the slabbing of unconsolidated cores. However, this second method has the disadvantage of always requiring the use of a liquid lubricant (such as water, kerosene, brine solutions or the like) between the knife blade and the core. A lubricant is necessary not only to prevent the knife from sticking as it passes through the core, but also to prevent drag on the blade from distorting the interior surface of the slab as the cut is being made. The use of a lubricant is undesirable because of its tendency to distort both the physical and chemical integrity of the core interior. Additionally, the knife used in this second method is incapable of splitting larger rock fragments which may be contained in the cores.

A third method of slabbing is used in which the sample is first frozen in dry ice. After freezing, the plastic tube is removed from the core by the application of several sharp hammer blows which shatter the brittle, frozen plastic. The still frozen core is then wrapped with aluminum foil and placed within a thick-walled cardboard tube. An immobilizing compound, such as epoxy resin, is then poured into the tube in order to cast the core and the core is left to cure. After the curing heat subsides, the core is refrozen.

The frozen and immobilized core is then oriented vertically and divided by drawing a radial blade saw down through the length of the core. The resulting slab is recovered as it falls to the side.

This third method may be used for slabbing core material which is unconsolidated, since the loose contents of the core are held intact by freezing and immobilization. Use of a radial blade saw also enables the slabbing of samples which contain large rock fragments. However, this third method is both time consuming and expensive, requiring the use of both an immobilizing compound and a liquid coolant (such as liquid nitrogen) to dissipate the heat generated and overcome the friction encountered by the radial blade saw. Disturbance to the core interior may occur at several points during the process, including the freezing and immobilizing of the core and the recovery of the unsupported vertical slab as it falls away from the remaining core.

An objective of the present invention is therefore to provide methods and apparatus for slabbing any sample, including one in which the core material is friable, unconsolidated, or contains large rock fragments, without distorting the physical structure or contaminating the chemical composition of the core.

A further objective of the present invention is to provide methods and apparatus by which a sample may be slabbed directly as it is received from the field with minimum disturbance to the interior of the core.

A further objective of the present invention is to provide a method and apparatus for slabbing which does not require the use of liquid coolants or liquid lubricants.

A further objective of the present invention is to provide a method and apparatus for slabbing which does not require that the sample be frozen or immobilized prior to being slabbed.

A further objective of the present invention is to provide a slabbing apparatus which is simple and inexpensive to construct and is reliable in operation.

SUMMARY OF THE INVENTION

In accordance with the present invention, these and other objectives are achieved by providing a bandsaw blade having a horizontally oriented cutting edge. A horizontally oriented sample is divided into an upper and lower portions by advancing the sample against the bandsaw blade. The upper portion of the slab thereby created is supported by a receiving tray positioned immediately adjacent and to the rear of the bandsaw blade.

BRIEF DESCRIPTION OF THE DRAWINGS

A detailed description of the invention will be made with reference to the accompanying drawings, wherein like numerals designate corresponding parts in the several figures.

DESCRIPTION OF THE PREFERRED EMBODIMENT

The following detailed description is of the best presently contemplated mode of carrying out the invention. This description is not to be taken in a limiting sense, but is made merely for the purpose of illustrating the general principles of the invention. The scope of the invention is best defined by the appended claims.

Referring to FIGS. 1, 2, 3 and 4, the invention includes a bandsaw main frame 2 which houses a bandsaw blade 4 having a continuous circulating cutting edge 6. Any one of a number of commercially available bandsaw machines may be used for purposes of the present invention, including, for example, the Zephyr model number 75-3620 Do-All bandsaw machine manufactured by the Do-All International Corporation, a subsidiary of the Do-All Company of Des Plaines, Ill.

Figure 4:
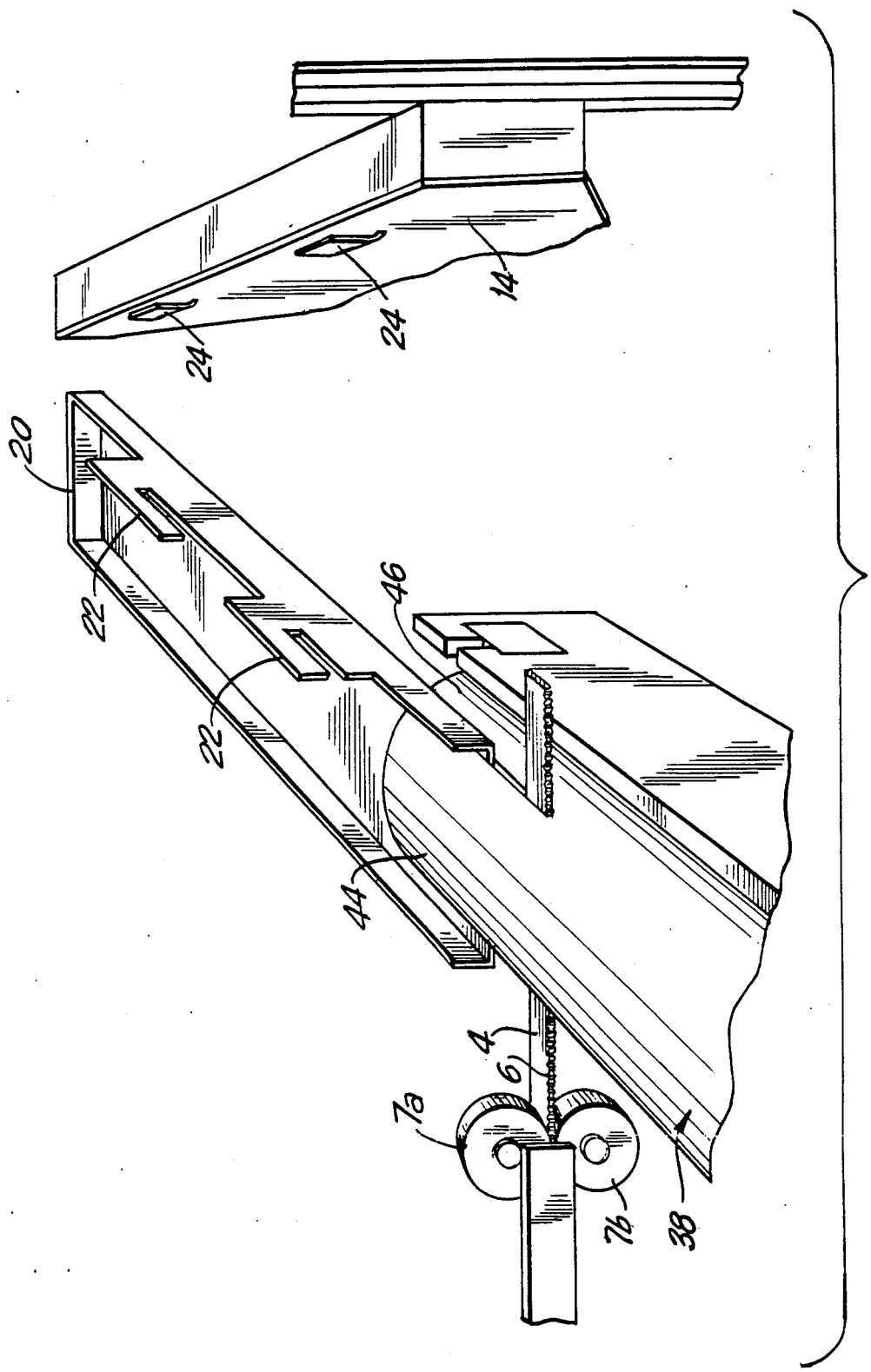
FIG. 4 is a fragmentary perspective view showing details of one embodiment of the slab receiving means of the present invention.

The bandsaw main frame 2 is positioned so that the cutting edge 6 of the bandsaw blade 4 is oriented horizontally. The cutting edge 6 of the bandsaw blade 4 may be composed of any of a number of materials which are commonly used for cutting minerals or metals, including diamond, tungsten, carbide, spring tempered steel, carborundum, and silicon carbide. A pair of rollers 7a,b serve to guide and stabilize the horizontal bandsaw blade 6 immediately prior to its contact with the sample 38 (FIG. 4).

The use of a horizontal bandsaw blade in the present invention provides several advantages over the cutting means (knives, wires, radial blades, etc.) used in the prior art. One such advantage is that the bandsaw blade of the present invention is capable of cutting through extremely hard objects, thereby enabling the slabbing of cores containing large rock fragments.

Another advantage of the bandsaw blade is that the frictional heat generated by contact between the sample and the cutting edge during slabbing is dissipated along the entire length of the bandsaw blade. Experience has shown that, if the circumferential length of the bandsaw blade is sufficiently large, the heat is adequately dissipated by the bandsaw blade alone and the need for additional liquid coolants or lubricants to maintain the blade at a safe operating temperature is completely eliminated. This in turn eliminates the undesirable core distorting effects associated with such liquid coolants and lubricants. In the preferred embodiment, the circumferential length of the bandsaw blade 4 is approximately nineteen feet. However, smaller bandsaw machines having proportionately small blades of eight feet may be employed in the invention. The determining factor is whether the heat dissipating surface area of the blade is sufficient to prevent the temperature of the blade from exceeding its maximum safety limits. The amount of heat generated and therefore to be dissipated, will depend upon the size and composition of the samples as well as the type and condition of the cutting edge. Fluid coolants such as liquid nitrogen could be employed.

Still another advantage of a horizontally oriented bandsaw blade is that the surface of the blade serves to support the upper portion of the core slab immediately after the slab is separated from the sample, but before the slab is subsequently contacted and supported by a receiving tray in a manner described in further detail below. The use of horizontal cutting means thereby enables the entire slab to be fully supported during each step of the slabbing process, allowing the slabbing of samples containing friable-to-unconsolidated core material while preserving the integrity of the core interior.

Again referring to FIGS. 1, 2, 3 and 4, a horizontally oriented travel plate 8 is mounted perpendicular to the bandsaw main frame 2 so that the travel plate 8 straddles the bandsaw blade 4. The travel plate 8 is supported by a base plate 10 which is also mounted on the bandsaw main frame 2. The vertical position of the travel plate 8 with respect to the bandsaw blade 4 may be adjusted by means of a series of adjustment slots 12, thereby enabling slabs of varying thickness to be cut. The base plate 10 includes an upper edge 14 which extends several inches above the plane defined by the horizontal bandsaw blade 4.

Resting on the travel plate 8 is a sample holder 16. The sample holder 16 is configured to hold a sample in place as the sample is advanced against the bandsaw blade 4, so that the same relative angular orientation between the sample 38 and the bandsaw blade 4 is maintained throughout the slabbing operation. The sample holder 16 rests in a guide track 18 which runs along the length of the travel bed 8 in a direction perpendicular to the bandsaw blade 4. The guide track 18 allows the sample retained within the sample holder 16 to be advanced across the bandsaw blade 4 smoothly and evenly. As shown most clearly in FIGS. 4 and 5, a slab receiving tray 20 is disposed adjacent to and co-planar with the bandsaw blade 4. The receiving tray 20 may be secured in this position by attaching it to the upper edge 14 of the base plate 10 by means of tray hooks 22 which engage clips 24 attached to the upper edge 14.

One or more suction hoses 26 are positioned near the cutting edge 6 of the bandsaw blade 4. These suction hoses 26 are operationally connected to a remote vacuum source 28 and operate to remove from the cutting site extraneous material or "rock flour" which may be produced when the bandsaw blade 4 encounters brittle material in the sample 38. The partial vacuum produced by hoses 26 at the cutting site also causes a stream of air to act as a fluid coolant as it passes over the blade 4, supplementing the heat dissipating effect of the bandsaw blade 4. The need for applying undesirable liquid coolants of the prior art is thereby eliminated.

A slabbing operation in accordance with the above-described embodiment of the present invention may proceed as follows:

A sample 38 comprising a geological core 40 which is enclosed within a plastic tube 42 is placed on the sample holder 16, thereby orienting the longitudinal axis of the sample 38 so that it is substantially co-planar with, and perpendicular to, the cutting edge 6. The operation of the bandsaw blade 4 is initiated by closing a switch 50, which completes a circuit between the bandsaw motor 52 and a power supply (not shown). The operation of the vacuum source 28 attached to suction hoses 26 is also initiated at this time.

Figure 1:
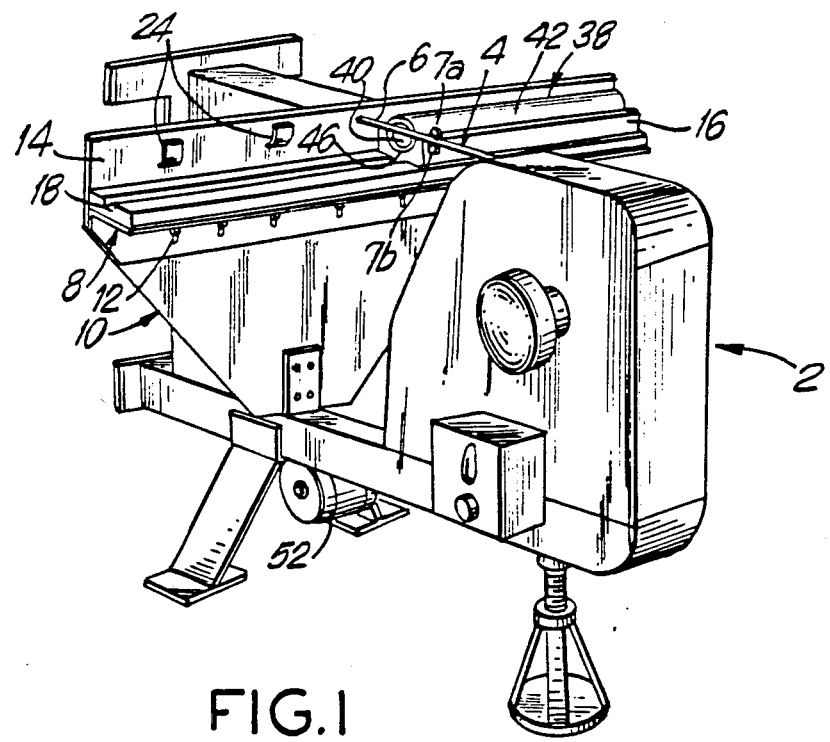
FIG. 1 is a perspective view of one embodiment of the present invention.
Figure 2:
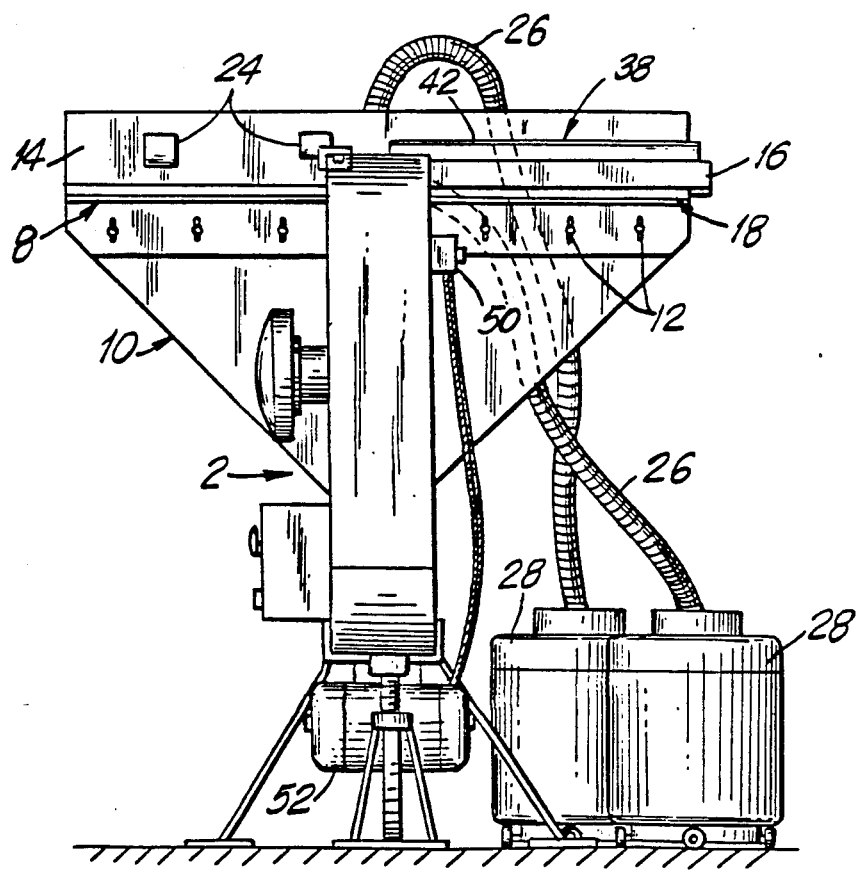
FIG. 2 is an end view of the embodiment shown in FIG. 1.
Figure 3:
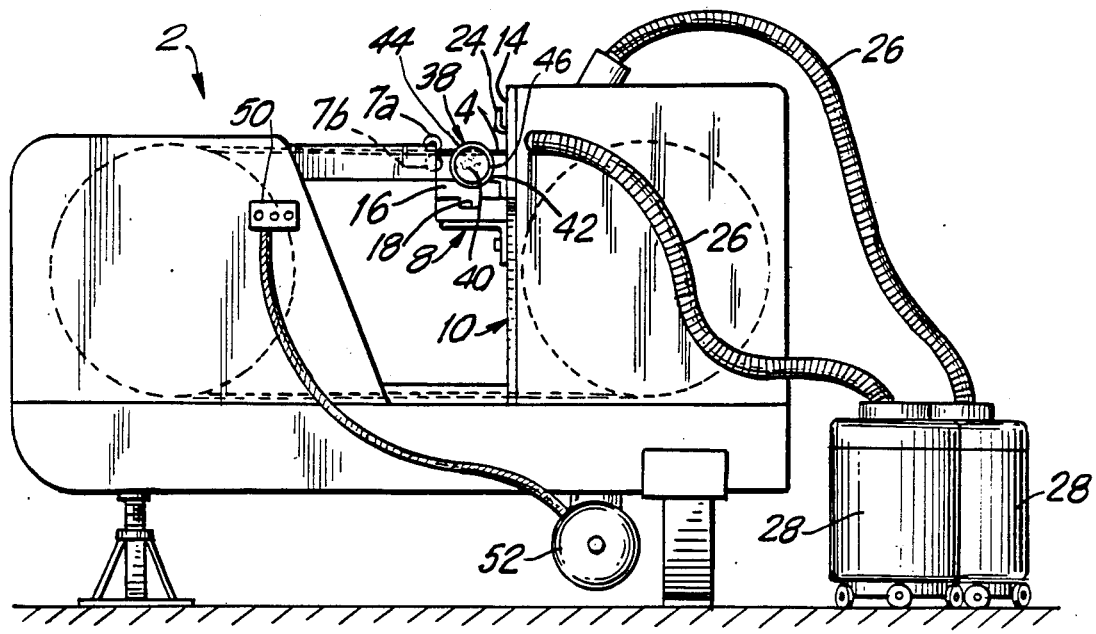
FIG. 3 is a side elevation of the embodiment shown in FIG. 1.
Figure 5:
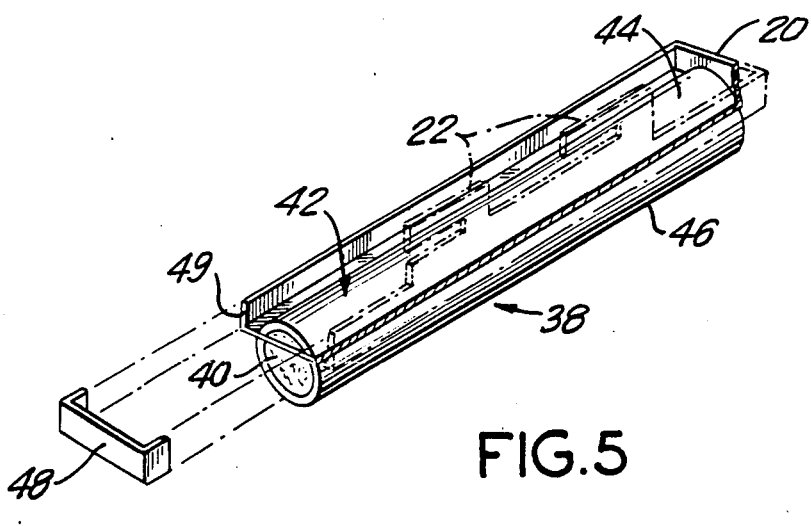
FIG. 5 is a perspective view showing the slab in relation to the receiving means.

The sample holder 16 is than advanced along guide track 18, thereby causing the sample 38 to come into contact with the cutting edge 6 of the circulating bandsaw blade 4. As sample holder 16 is advanced, the cutting action of the bandsaw blade 4 will divide the sample 38 along its longitudinal axis into two sections: an upper core section or "slab" 44 and a lower core section or "bulk" 46 (FIGS. 4 and 5).

The receiving tray 20 is positioned to receive the advancing core slab 44 immediately after its passes over the bandsaw blade 4. The advancing slab 44 is therefore always supported by either the bandsaw blade 4 or the receiving tray 20 which is positioned immediately to the rear of, and in close proximity to the blade 4. The surface integrity of even the most unconsolidated core is thereby preserved. Once the sample 38 has been completely divided, the receiving tray 20 contains the completed slab 44. The receiving tray 20 may be easily inverted to expose the fresh cut surface of the slab 44 for geological examination and photography.

In addition, if immobilization of the completed slab 44 is desired, a nonporous end cap 48 may be secured to the receiving end 49 of the receiving tray 20. A leak proof container is thereby created into which epoxy, plaster-of-paris, paraffin, or any other of a number of molding compounds may be poured in order to immobilize the slab 44.

The present invention may be embodied in other specific forms without departing from the spirit or essential characteristics thereof. For example, a sufficiently long horizontal reciprocating blade (similar to a rip-saw blade) may be used in substitution for the disclosed bandsaw blade. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. In the method for longitudinally dividing an elongated stratigraphic sample comprising a core enclosed within a tube to thereby expose the interior of said core, the improvement which comprises the steps of:
   orienting a cutting means comprising a continuous circulating cutting edge in a substantially horizontal plane,
   positioning the longitudinal axis of said sample in a plane substantially parallel with said cutting edge,
   bringing said sample and said cutting edge into contact with one another to thereby divide said sample into an upper section and a lower section,
   receiving said upper section as said sample is divided in a receiving means positioned immediately adjacent to and co-planar with said cutting means, and providing continuous and uninterrupted support for said upper section as said sample is divided, without deflecting said upper section from said lower section,
   whereby the physical integrity of the interior surface of the sectioned core is preserved.

2. The method of claim 1 which further comprises the step of immobilizing the upper section of the core after it has been divided.

3. The method of claim 2 which comprises applying an immobilizing compound to the upper section of the core while it is in said receiving means.

4. A sectioned core produced in accordance with the method of claim 1.

5. An interior surface of a core exposed in accordance with the method of claim 1.

6. The method of claim 1 wherein the cutting means has a sufficient heat dissipating area to maintain the temperature of the cutting means within its safe operating range.

7. The method of claim 6 wherein the cutting means comprises a bandsaw blade.

8. The method of claim 1 wherein the cutting means are supported on a stationary frame, and the sample is advanced into contact with the cutting means.

9. The method of claim 8 where the receiving means is maintained in a stationary position during the cutting and dividing of the sample.

10. The method of claim 1 wherein a stream of fluid coolant is passed over the cutting means.

11. The method of claim 10 wherein the stream of fluid coolant also provides an exhaust medium for removing extraneous core material generated by the cutting means.

12. The method of claim 1 which includes the further step of closing the receiving means to provide a container having a base and continuous upstanding walls to a height that exceeds that of the upper surface of the sectioned core sample.

13. The method of claim 3 in which the upper section of the core is immobilized by application of an immobilizing compound selected from the group of molding compounds consisting of epoxy, plaster-of-paris and paraffin.

* * * * *